US011417294B2

(12) United States Patent
Jiang

(10) Patent No.: US 11,417,294 B2
(45) Date of Patent: Aug. 16, 2022

(54) SYSTEMS AND METHODS FOR REMOTE INTERACTION WITH AN ENHANCED MONOCHROMATIC IMAGE PRESENTATION DEVICE

(71) Applicant: Armstel Inc., Plano, TX (US)

(72) Inventor: Simon Jiang, Allen, TX (US)

(73) Assignee: Armstel Inc., Plano, TX (US)

( * ) Notice: Subject to any disclaimer, the term of this patent is extended or adjusted under 35 U.S.C. 154(b) by 0 days.

(21) Appl. No.: 17/046,438

(22) PCT Filed: Apr. 12, 2019

(86) PCT No.: PCT/US2019/027316
§ 371 (c)(1),
(2) Date: Oct. 9, 2020

(87) PCT Pub. No.: WO2019/200315
PCT Pub. Date: Oct. 17, 2019

(65) Prior Publication Data
US 2021/0110789 A1    Apr. 15, 2021

Related U.S. Application Data

(60) Provisional application No. 62/657,317, filed on Apr. 13, 2018.

(51) Int. Cl.
*G09G 5/10* (2006.01)
*G16H 15/00* (2018.01)
(Continued)

(52) U.S. Cl.
CPC .............. *G09G 5/10* (2013.01); *A61B 5/742* (2013.01); *G16H 15/00* (2018.01); *G16H 30/20* (2018.01);
(Continued)

(58) Field of Classification Search
CPC ............ G09G 5/10; G09G 2320/0693; G09G 2340/14; G09G 2360/144;
(Continued)

(56) References Cited

U.S. PATENT DOCUMENTS 8,531,476 B1    9/2013    Jiang et al.
8,531,477 B2    9/2013    Jiang et al.
(Continued)

OTHER PUBLICATIONS

Written Opinion of the International Search Report from PCT/US2019/027316; dated Jul. 17, 2019; 5 pages.
(Continued)

*Primary Examiner* — Antonio A Caschera
(74) *Attorney, Agent, or Firm* — Haynes and Boone, LLP

(57) ABSTRACT

A system to calibrate, monitor, and communicate compliance reporting of monochromatic imagery on an image presentation device includes a local terminal in operative communication with a remote host. The local terminal includes an image presentation device, an application-specific integrated circuit ("ASIC"), and a terminal application in communication with the ASIC. The terminal application
(Continued)

is configured to initiate a verification task, via the ASIC, pertaining to an operating condition of the image presentation device and to communicate a verification report about a result of the verification task to a remote host. A system provides a mechanism to remotely monitor and calibrate medical imaging image presentation device and diagnosis devices to certify diagnosis quality and retain trustworthy data for legal compliance.

23 Claims, 5 Drawing Sheets

(51) Int. Cl.
| | |
|---|---|
| *G16H 30/20* | (2018.01) |
| *G16H 50/20* | (2018.01) |
| *G16H 30/40* | (2018.01) |
| *G16H 40/40* | (2018.01) |
| *A61B 5/00* | (2006.01) |

(52) U.S. Cl.
CPC ............ *G16H 30/40* (2018.01); *G16H 40/40* (2018.01); *G16H 50/20* (2018.01); *G09G 2320/0693* (2013.01); *G09G 2340/14* (2013.01); *G09G 2360/144* (2013.01); *G09G 2360/145* (2013.01); *G09G 2370/02* (2013.01); *G09G 2380/08* (2013.01)

(58) Field of Classification Search
CPC ......... G09G 2360/145; G09G 2380/08; G16H 15/00; G16H 30/20; G16H 50/20; G16H 30/40; G16H 40/40; A61B 5/742
See application file for complete search history.

(56) References Cited

U.S. PATENT DOCUMENTS

| | | |
|---|---|---|
| 9,157,951 B1 | 10/2015 | Jiang |
| 2007/0055143 A1 | 3/2007 | Deroo et al. |
| 2008/0161661 A1* | 7/2008 | Gizewski ............. A61B 5/0064 600/306 |
| 2011/0098957 A1* | 4/2011 | Zaidi ....................... G01J 3/027 702/85 |
| 2014/0247341 A1 | 9/2014 | Jackson |

OTHER PUBLICATIONS

International Search Report from PCT/US2019/027316; dated Jul. 17, 2019; 2 pages.
International Preliminary Report on Patentability, PCT/US2019/027316; dated Jul. 17, 2019; 6 pages.
PCT International Application No. PCT/US19/27316, International Search Report of The International Searching Authority, dated Jul. 17, 2019, 2 pages.
PCT International Application No. PCT/US19/27316, Written Opinion of The International Searching Authority, dated Jul. 17, 2019, 5 pages.

* cited by examiner

SYSTEMS AND METHODS FOR REMOTE INTERACTION WITH AN ENHANCED MONOCHROMATIC IMAGE PRESENTATION DEVICE

RELATED APPLICATIONS

This patent application is a 371 International of Application No. PCT/US19/27316, filed Apr. 12, 2019, which claims priority to and the benefit of filing date of U.S. Provisional Patent Application 62/657,317 entitled "SYSTEMS AND METHODS FOR REMOTE CALIBRATION AND/OR REMOTE MONITORING OF AN ENHANCED MONOCHROMATIC DISPLAY DEVICE", filed Apr. 13, 2018 which is incorporated by reference herein in its entirety.

FIELD

The present disclosure relates generally to the field of human information display and, more particularly, to systems and methods for calibrating, monitoring, and reporting compliance of electronic image presentation devices in relation to a standard.

BACKGROUND

Often times, particularly in the medical field, it is necessary to display one or more images on an image presentation device. For example, X-ray, MRI or CT imagery from various modalities may be reviewed by a doctor or medical technician for the purpose of diagnosing a medical condition. A variety of factors related to an image presentation device may affect the quality of an image being displayed such as resolution, luminance, shading, color, etc. In order to ensure information contained in the imagery is presented to a user in a format having a level of quality sufficient for proper interpretation and diagnosis, imaging standards are developed and implemented. An imaging standard may include, for example, a generally-accepted or formal industry or regulatory standard ("standard"). Compliance with such standards may be necessary to satisfy the standard of care or to avoid misdiagnoses.

SUMMARY

Embodiments of the invention are best summarized by the claims that follow the description.

Consistent with some embodiments, a system comprises a local terminal in operative communication with a remote host. The local terminal comprises an image presentation device, an application-specific integrated circuit ("ASIC"), and a terminal application in communication with the ASIC. Additionally, a local terminal may comprise one or more sensors or meters. The terminal application is configured to initiate a verification task, via the ASIC, pertaining to an operating condition of the image presentation device, which may be measured by a meter or sensor in some embodiments, and to communicate a verification report about a result of the verification task to a remote host.

Consistent with some embodiments, a method comprises providing a local terminal in operative communication with a remote host. The local terminal includes an image presentation device, an application-specific integrated circuit ("ASIC"), and a terminal application stored at the local terminal and operable to provide instructions to the ASIC. The method further includes receiving a verification instruction from the remote host at the local terminal. In response to the verification instruction, the method includes performing, via the ASIC, a verification task on the local terminal, the verification task pertaining to an operating condition of the image presentation device, which may be measured using a meter or sensor. The method also includes transmitting a verification report based on a result of the verification task to the remote host via at least one network using internet protocol.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
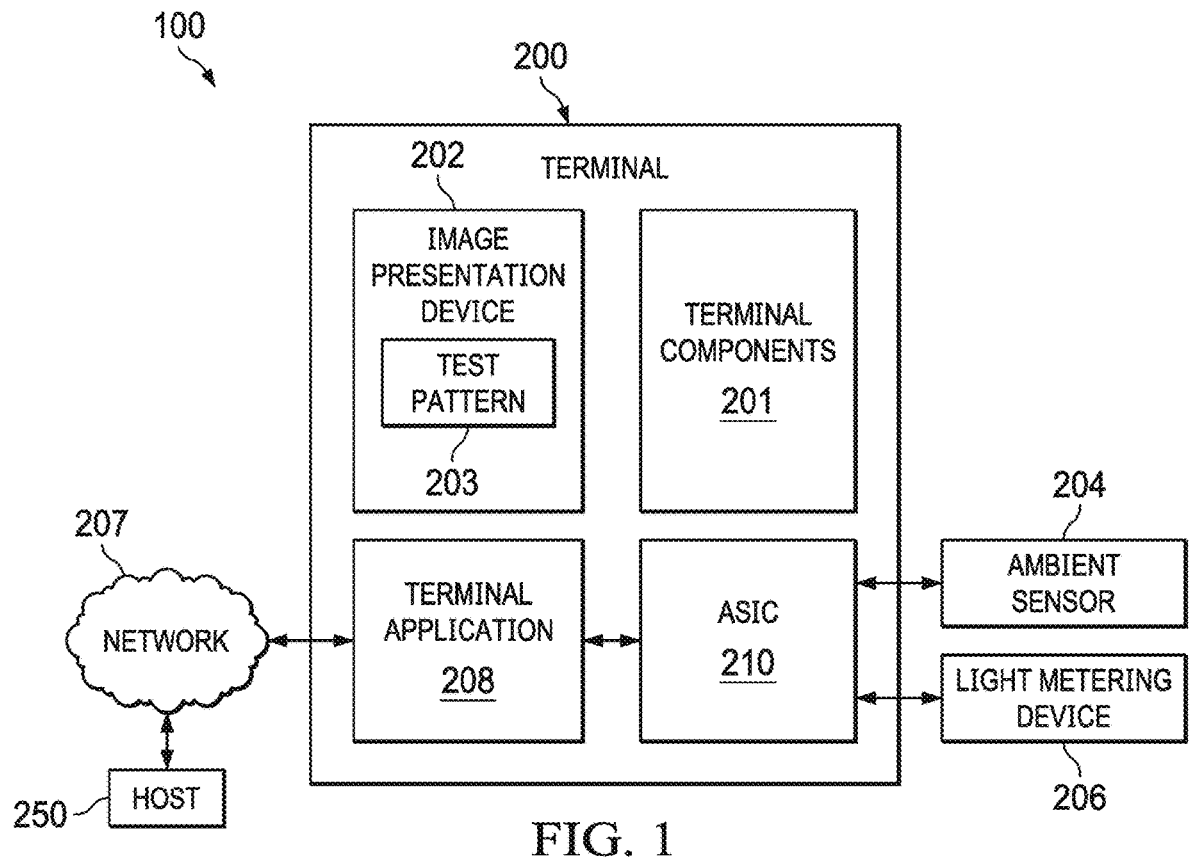
FIG. 1 is a simplified block diagram of a system for verifying conformance of an image presentation device with a standard.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Various embodiments of utilities (systems, methods, and apparatuses) related to remote monitoring and calibration of image presentation devices are described herein.

FIG. 1 is a block diagram of a system 100 for verifying conformance of an image presentation device with a standard. The system may include local terminal 200 coupled to a remote host 250 and to one or more sensors 204, 206. The local terminal 200 may include an image presentation device 202 and an application-specific integrated circuit (ASIC) 210, and one or more terminal components 201 such as processors, user input devices, and/or memory storage devices. Sensors 204, 206 may be integrated with or coupled to the local terminal 200 by wired or wireless connections.

As used herein, the term "image presentation device" may refer to any apparatus, device, or system which is capable of visually displaying, projecting or otherwise presenting one or more images to a viewer. For example, a local terminal comprising an image presentation device may include a laptop, a camera, a television, an all-in-one computer, a tablet, a smartphone, a projector, or the like. For example, an image presentation device may include an LCD (Liquid Crystal Display), PDP (Plasma Display Panel), LED (Light Emitting Diodes), OLED (Organic LEDs), DLP (Digital Light Processing), LCoS (Liquid Crystal on Silicon), SED (Surface-conduction electron-Emitter Display), FED, (Field Emission Display), MEMS (Micro-electro-mechanical systems), laser systems, projection systems, and many others. An image presentation device may include an image capturing system such as a camera, a CT scanner, an MRI machine, X-ray machine, etc., which includes a means of presenting a captured image to a user.

As described in more detail below, in one embodiment, system 100 can be configured to cause a target test image presentation device to generate test patterns 203 and to determine whether the target test image presentation device conforms to a predetermined standard based on characteristics of emissions generated as target test image presentation device generates the test patterns. This process may be initiated by a remote host for compliance verification.

Generally, the predetermined standard is any suitable standard and/or benchmark. In one embodiment, the standard is a generally-accepted or formal industry or regulatory standard. In one embodiment, the predetermined standard is the Digital Imaging and Communications in Medicine (DICOM) standard for handling, storing, printing, and transmitting information in medical imaging. In one embodiment, the predetermined standard is the DICOM Part 14 Grayscale Standard Display Function standard. The National Electrical Manufacturers Association (NEMA) created the DICOM standard in part to ensure that diagnostic images appear the same, whether viewed via print, film, or electronic display.

In the illustrated embodiment, image presentation device 202 may be a target test image presentation device, and the system 100 is configured to determine whether image presentation device 202 conforms to a predetermined standard. As used herein, the "target test image presentation device" is sometimes referred to as a "target image presentation device," "test image presentation device," "target image presentation device." As used herein, the determination of whether an image presentation device conforms to a predetermined standard is sometimes referred to as a "test," "verification," or "inspection." Further, one or more components of a system that determines whether an image presentation device conforms to a predetermined standard are sometimes referred to herein as a "tester" or "inspector." Further, one or more components of a system that determines whether an image presentation device conforms to a predetermined standard may be referred to by the trade name "Calispector™."

In this embodiment, the local terminal 200 may be a tablet computer, a laptop, computer, a desktop computer, a monitor, or any other type of computing device in wired or wireless communication with the remote host 250. In one embodiment, the image presentation device 202 of the local terminal 200 may display images in color or in enhanced grayscale. As used herein, "grayscale," means any monochromatic range of shades. For ease of illustration, the disclosed embodiments are described with respect to a gray "grayscale," a range of shades based on a base color of gray. One skilled in the art will understand that the disclosed embodiments can be converted to operate with any base color so as to produce a range of shades in that base color. For example, in one embodiment, an image presentation device output is configured as a red grayscale. As such, unless otherwise indicated, "grayscale" and "monochromatic" are used herein substantially interchangeably.

The image presentation device 202 may include an array of pixels or other suitable display configured to produce images visible to the human eye. Generally, the image presentation device 202 may generate images based on input received from a variety of modalities such an imaging apparatus (e.g., X-ray, CT, etc.) or other system to which image presentation device 202 couples or is in operative communication with, as described in more detail below.

In some embodiments, the image presentation device 202 may be tested by generating test images and evaluating the test images using a testing meter such as the light metering device 206. Test results received from the light metering device 206 may be compared to a standard. In some embodiments, the remote host 250 may send a verification instruction via a network to the local terminal 200. The verification instruction may provide an indication of a particular calibration or test to be performed, or data to be retrieved from memory of the local terminal 200 and transmitted to the remote host 250. In various embodiments, the light metering device may be coupled to the local terminal 200 by a cable such as a standard USB cable, integrated with the local terminal 200 in a common housing, or by a wireless connection. In one embodiment, light metering device 206 couples to the image presentation device 202, receives emissions from image presentation device 202 and sends signals to the ASIC 210 based on the emissions. In one embodiment, light metering device 206 is a standalone lux meter (e.g., Simlux™) coupled to the local terminal 200 using an external cable such as a USB cable. In another embodiment, light metering device 206 is housed in the local terminal 200, or image presentation device 202 of the local terminal 200, and connected to an internal component such as the ASIC 210 via an internal connection, such as a Universal Asynchronous Receiver/Transmitter (UART) cable. In an embodiment, a lux meter may measure a luminosity characteristic of emissions received by the lux meter. In some embodiments, the testing may be performed automatically without user input based on a verification instruction received at the local terminal 200 from the remote host 250. In other embodiments, the testing may be initiated by a user operating the local terminal 200.

In the illustrated embodiment, test patterns 203 are test patterns and/or images (or activated pixel patterns based on information stored in a graphics buffer, for example) generated by image presentation device 202. Generally, test patterns 203 generate emissions that can be analyzed to determine whether image presentation device 202 is generating images in conformity with a standard. In one embodiment, test patterns 203 are presented in a standard monitor window. The test patterns 203 may be positioned so that the emissions generated by test patterns can be captured by the light metering device 206. In some embodiments, results from light metering device 206 may generate a report for display on the local terminal 200. In some embodiments the report display can include graphs, text, and/or other visual representations of information, in any combination. In other embodiments, rather than displaying report data to the user via a report display, the report information may be transmitted via a network to the remote host 250 for secure storage or centralized evaluation. This may ensure report data is unaltered at the local terminal 200 and is trustworthy for legal compliance. In this regard, report data may be encrypted by the ASIC 210 as it is recorded.

Remote host 250 may be a centralized control station, which may include a server, configured to communicate with one or more local terminals via one or more communications networks 207 which may be wired or wireless. In some embodiments, communications networks may include a telecommunications network, cloud, ethernet, Internet, intranet, cable or fiber optic lines, WiFi, or a combination thereof. The remote host 250 may transmit verification instructions to the local terminal 200 and receive verification reports from the local terminal 200. Verification reports may include any data related to one or more operating conditions of a local terminal 200 with regard to a standard or other compliance-related concerns. Verification instructions may include a command or set of commands for a local terminal 200 to perform a verification task and/or transmit a verification report immediately or at some future time. For example, remote host 250 may include a server disposed at a medical facility, the server being in operative communication with a plurality of local terminals 200 in the facility (e.g., tablet computers used to review X-ray images) via a wireless network. The remote host 250 may send a verification instruction to each local terminal 200 in communication therewith to perform a verification task related to an operating condition of the local terminal on a certain date at a certain time. At the scheduled time, and in response to the verification instruction, the local terminal may initiate a verification task. A verification report containing data from the verification task may be generated and transmitted to the remote host 250 for storage and/or analysis. Verification reports may be generated, stored at the local terminal 200, transmitted, and/or stored at the remote host 250 in a secure manner to ensure the integrity of the information therein. In this regard, a proprietary encryption structure or internal protocol may be implemented by the ASIC 210 operating on local terminal 200. The ASIC 210 may be configured in a manner that prevents users or malicious parties from altering data collected by the ASIC 210. In this regard, verification reports may be considered a trustworthy source of records of operating conditions of the local terminal 200.

Verification tasks may include detecting or confirming any operating condition of a local terminal such as, but not limited to: calibrating the image presentation device or verifying the image presentation device conforms to a DICOM standard using a light metering device; determining a level of ambient lighting at the image presentation device to ensure proper conditions for making a diagnosis from an image; compiling usage data related to operation of the local terminal into a report; verifying hardware and/or software settings; reviewing diagnostic quality control data of the local terminal; determining and reporting a location of the local terminal; calculating a Barten curve of the local terminal; recording an operating status of the local terminal (e.g., powered on, currently displaying diagnostic imagery, etc.); and/or reporting a service history of the local terminal (e.g., last date of inspection or repair). It should be appreciated that this is not an exhaustive list and verification tasks may include the processing of any information that may be useful in analyzing the conditions in which or at which a local terminal is operating. Such information may be beneficial, for example, for verifying compliance with standards, for legal defense of a malpractice claim by establishing a secure record of appropriate image quality and environmental conditions for diagnostics, etc.

The remote host 250 may include software for DICOM calibration scheduling, for checking a status of one or more local terminals, for altering or verifying DICOM compliance settings at the remote host 250 or at the local terminal 200, for implementing remote medical diagnosis services, and any other functions beneficial for ensuring local terminals remain in compliance with standards, regulations, policies, etc. For example, a remote host 250 may sent queries to the local terminal 200 for status, historical data, machine data, current operations, location, services history, priority, etc. In response to a query, the local terminal 200 may retrieve and transmit information requested in the query back to the remote host 250 for recording.

In additional to queries, a remote host 250 may also send requests to local terminals 200. A request may elicit the local terminal 200 to perform a function beyond simply retrieving and sending data. For example, a request from a remote host 250 may require the local terminal 200 to perform DICOM calibration, verify an ambient luminance, power on or power off, toggle into or out of a DICOM operating mode (e.g., in which the image presentation device is configured to operate in a performance mode which complies with DICOM requirements), start or stop a service, etc. As used herein, the term "verification instruction" may refer to a query and/or a request sent from a remote host to a local terminal, and the term "verification report" may refer to any information sent from a local terminal to a remote host. Verification instructions and verification reports may be encoded or encrypted before transmission and decoded or decrypted upon receipt. This may be advantageous for complying with Health Insurance Portability and Accountability Act ("HIPAA") requirements.

A remote host 250 may schedule queries and requests for future data collection. For example, an administrator may input a policy into a remote host that DICOM compliance should be verified on a periodic basis. In response, the remote host 250 may send verification instructions to local terminals 200 scheduling future compliance inspections accordingly, or the remote host 250 may wait until a scheduled time and then send verification instructions eliciting an immediate response from local terminals. The remote host 250 may schedule queries and requests for local terminals 200 pertaining to monitoring, calibration, services, etc. Records of queries and requests may be stored at the remote host 250. These records may include the information that was requested from the local terminal 200, the processes that were instructed to be performed by the local terminal 200, the time at which the verification instruction was sent, and a time at which a confirmation of receipt of the verification instruction was received at the remote host from the local terminal 200.

Further, a remote host 250 may be tasked with controlling medical diagnosis services. For example, a remote host 250 may be operable to alter or confirm settings on a local terminal to ensure medical diagnoses are performed under optimal conditions. Specifically, as an example, a remote host 250 may send a verification instruction to the local terminal 200 which requires diagnosis services to halt operations on the local terminal if certain conditions are not satisfied, such as if the local terminal image presentation device has not been calibrated for an unacceptable period of time or if ambient lighting conditions at the image presentation device are not optimal for viewing medical images. In this regard, remote host 250 may alter conditional requirements from time to time to maintain local terminals 200 in compliance with standards.

Verification processes may be initiated and/or controlled by a terminal application 208 operating on the local terminal 200. The terminal application 208 may be provided by the manufacturer of the ASIC 210, or by the manufacturer of the image presentation device 202, and may include instructions for operating the ASIC 210 in a manner that ensures compliance with one or more standards. Furthermore, the terminal application 208 may control the presentation of images on the image presentation device 202, for example, by providing a graphic user interface through which users may access and view images subject to quality control based on standards.

The terminal application 208 may receive verification instructions from the remote host 250 and implement processes (e.g., verification tasks such as testing, monitoring, calibrating, service, reporting, etc.) according to the verification instructions. Various tasks that may be performed to evaluate the image presentation device are described in U.S. Pat. Nos. 8,531,476, 8,531,477, and 9,157,951, each of which is incorporated by reference herein, in its entirety. The terminal application 208 communicates with the ASIC 210 to perform the requested verification tasks. Upon completion of, or periodically during, the appropriate verification task(s), the terminal application 208 is responsible for sending verification reports to the remote host 250. Typically, these communications are transmitted via Internet protocol over one or more networks.

The terminal application 208 may be stored on a memory module (e.g., one of the terminal components 201) of the local terminal which is separate from the ASIC 210 or may be stored within memory of the ASIC 210, for example, as firmware. By providing the terminal application 208 as firmware, it may be possible to improve data security and prevent unauthorized tampering or altering of data that is reported to the remote host 250.

Figure 2:
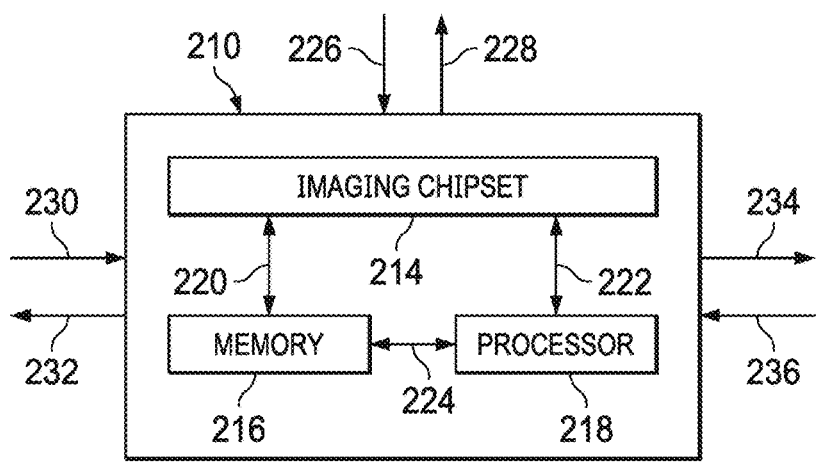
FIG. 2 is a simplified block diagram of an imaging chipset and flow of data according to an embodiment.

FIG. 2 is a simplified block diagram illustrating the ASIC 210 and the flow of data into and out of the ASIC 210, according to an embodiment. In one embodiment the ASIC 210 maybe a system-on-a-chip ("SoC") including an imaging chipset 214, memory 216, and processor core 218. In some embodiments, the imaging chipset 214 may be an intelligent medical imaging chipset configured to control operation of the processor core 218, at least during one or more operating modes of an image presentation device in which a standard, such as a DICOM standard, is applicable. The processor core 218 may comprise a RISC-V or ARM Cortex-M core, although these specific devices are exemplary only and should not be considered limiting. Any suitable processing core may be used. Control data is exchanged between imaging chipset 214, memory 216, and processor core 218 via communications channels 220, 222, and 224 which may be integrated into ASIC 210. The ASIC 210 may receive functional requests from the terminal application 208. In this regard, functional requests may be any instruction received from the terminal application 208 which instructs the ASIC 210 to perform a specified function. Frequently, functional requests are sent by the terminal application 208 in response to the terminal application receiving a verification instruction from the remote host. Functional requests may include instructions to perform a DICOM inspection, calibration, ambient luminance check, DICOM mode control, machine data reading, etc. The ASIC 210 may be configured to communicate with other local terminal components 201 such as, but not limited to, speakers, power controllers, ambient light sensors, light metering devices, graphics cards, etc., for performing verification tasks. Additionally, the ASIC 210 may be tasked with performing system maintenance and refreshing data. In some embodiments, ASIC 210 may comprise separate and distinct components that are in operative communication to collectively perform the functions described in relation to ASIC 210. These distinct components may include any suitable hardware, chipsets, software, and the like.

Digital imagery from an imaging apparatus may be provided to ASIC 210 via any suitable communications protocol such as Mobile Industry Processor Interface ("MIPI"), Display Series Interface ("DSI"), Embedded DisplayPort ("eDP"), low-voltage differential signaling ("LVDS") through input channel 230, or a standard video interface such as Digital Visual Interface ("DVI"), DisplayPort ("DP"), WiFi, USB, etc. The digital imagery may be processed by the imaging chipset 214 to ensure compliance with appropriate standards and transmitted to the image presentation device 202 for viewing by a user through output channel 234.

Verification data, such as usage data or testing results from the ambient sensor 204 or light metering device 206, may be received by ASIC 210 through input channel 236. Processor core 218 may generate a verification report based on the verification data and store the verification report in memory chipset 216. Verification instructions 226 may be received at the ASIC 210 from the terminal application 208 of FIG. 3 running on the local terminal 200. Similarly, verification reports 228 may be transmitted through an output channel 232 to the remote host 250 via the terminal application 208 based on instructions received at the ASIC 210 from the terminal application 208.

Figure 3:
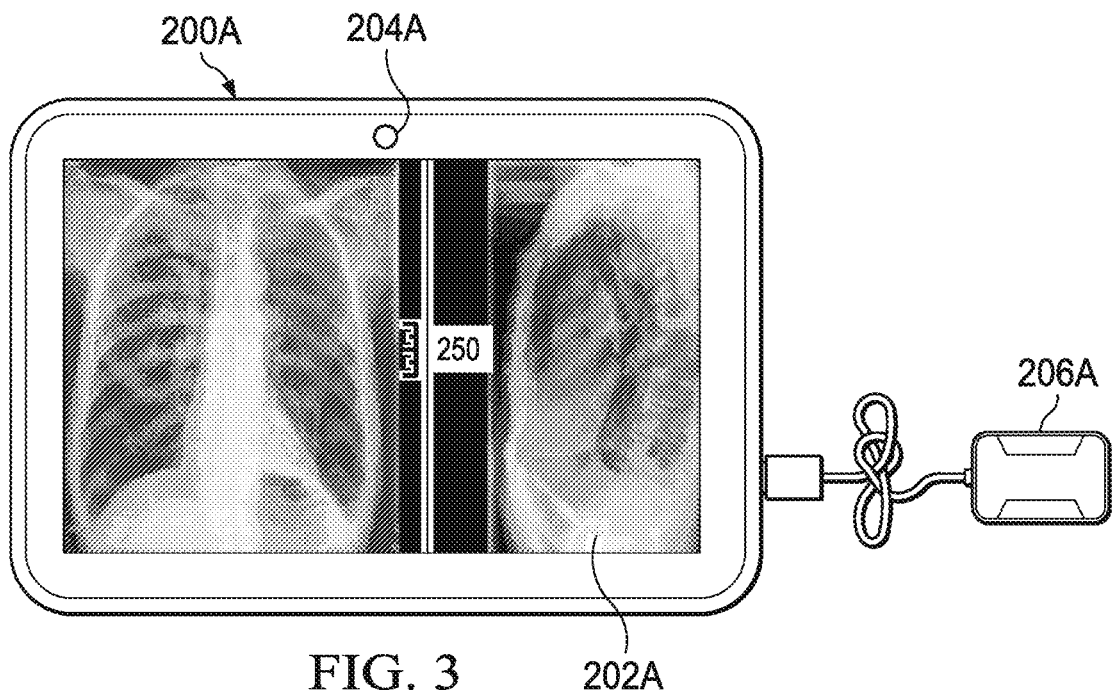
FIG. 3 illustrates a local terminal including a light metering device in accordance with an embodiment of the present disclosure.

FIG. 3 illustrates an example of the local terminal 200A (which may be substantially similar to local terminal 200 with the differences or enhancements as described) including a light metering device 206A in accordance with an embodiment of the present disclosure. In the illustrated embodiment, local terminal 200A is a tablet computer (e.g., an iPad®) with an integrated image presentation device 202A. It should be appreciated that a local terminal may be any computing device with an image presentation device capable of presenting imagery in a quality sufficient for compliance with a standard, such as but not limited to, a PC tower with separate monitor, a laptop computer, a phone, an all-in-one computer, etc. A local terminal may include or may be couplable to hardware accessories such as a speaker, a power control, a mouse or keyboard, etc.

Local terminal 200A may also include or be coupled to an ambient sensor 204A which may be any suitable sensor for detecting an ambient lighting condition, such as luminance, in the environment surrounding the local terminal 200A. In the illustrated embodiment, the ambient sensor 204A is a group of luminance sensors (e.g., a camera) provided by the manufacturer but which is selectably controllable by an imaging chipset (e.g., imaging chipset 214) and/or processor core (e.g. processor core 218) during use of the ambient sensor 204A for a verification task. The imaging chipset may take over control of the image presentation device from or coordinate control with an alternative processing core during verification tasks discussed in more detail below. That is, a dedicated processing core may be provided, such as on an ASIC of the local terminal 200A, to perform verification tasks on the local terminal 200A, but when verification tasks are not actively underway, a second processing core may be responsible for performing standard functions of the local terminal 200A such as accessing email, web browsing, etc. The dedicated functionality of the ASIC may ensure compliance with standards and prevent tampering with reporting records.

Light metering device 206A may be coupled to local terminal 200A either wirelessly or via a cable, for example, a USB cable. The light metering device 206A may be a lux meter having a test array of light sensors that can be disposed on or in close proximity to image presentation device 202A to measure a luminance of the image presentation device 202A. For example, the luminance or other visual characteristic of the image presentation device 202A may be determined with light metering device 206A during calibration of the image presentation device 202A or during a verification task to ensure compliance of the image presentation device 202A with a standard. It should be appreciated that light metering device 206A may be of any suitable size and shape to perform detection of an operating condition, such as luminance, of image presentation device 202A. In some embodiments, light metering device 206A may be integrated into the local terminal 200A rather than being a separate device that is couplable to the local terminal.

During a verification task such as inspection or calibration, the image presentation device 202A may produce a test output to be read by the light metering device 206A. The test output may cover the entire display area of the image presentation device 202A such that the image presentation device is not available for displaying medical images or other applications but must be dedicated to the verification task. Alternatively, the test output may be presented only in a test window that occupies only a portion of the display area of the image presentation device 202A such that the remainder of the display area may continue to be used by a viewer even during the verification task.

Figure 4:
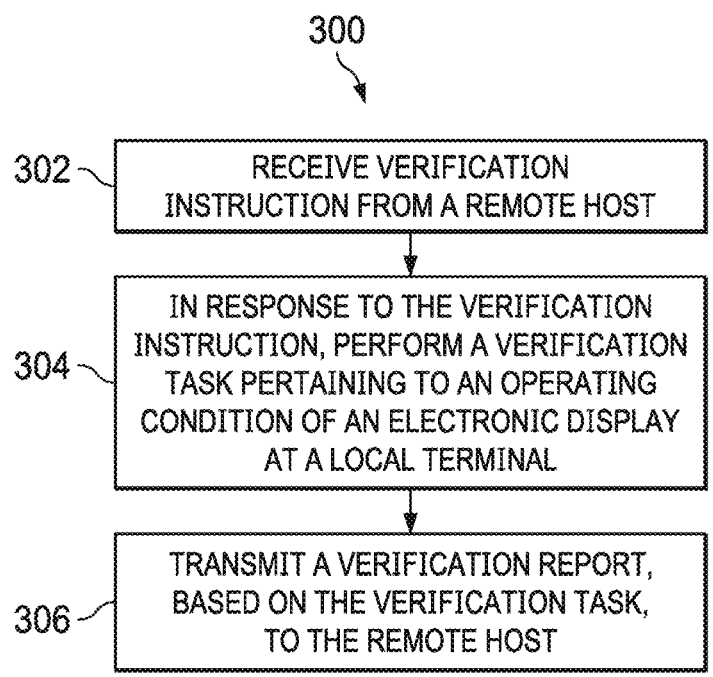
FIG. 4 illustrates a method for providing a verification from a local terminal to a remote host 250.

FIG. 4 is flowchart illustrating a method 300 for providing a verification from a local terminal (e.g., 200, 200A) to a remote host 250. The method 300 is illustrated as a set of operations or processes 302 through 306. Not all of the illustrated processes 302 through 306 may be performed in all embodiments of method 300. Additionally, one or more processes that are not expressly illustrated in FIG. 4 may be included before, after, in between, or as part of the processes 302 through 306. In some embodiments, one or more of the processes 302 through 306 may be implemented, at least in part, in the form of executable code stored on non-transitory, tangible, machine-readable media that when run by one or more processors may cause the one or more processors to perform one or more of the processes. In one or more embodiments, the one or more of the processes may be performed by the local terminal 200, 200A.

At a process 302, a verification instruction may be received from a remote host at a local terminal. The verification instruction may include a request to conduct a task including a status query, a location query, data query, a functional request, a service request, or an operational request. In some embodiments, the request may include instructions to conduct a particular calibration or test. The verification instruction may, for example, include a request to retrieve information from memory of the local terminal 200 and transmitted to the remote host 250.

At a process 304, a verification task may be performed (e.g., at the local terminal 200, 200A) in response to the verification instruction. The verification task may pertain to an operating condition of the image presentation device (e.g., 202, 202A at the local terminal. Verification tasks may include detecting or confirming any operating condition of a local terminal such as, but not limited to: calibrating the image presentation device or verifying the image presentation device conforms to a DICOM standard using a light metering device; determining a level of ambient lighting at the image presentation device to ensure proper conditions for making a diagnosis from an image; compiling usage data related to operation of the local terminal into a report; verifying hardware and/or software settings; reviewing diagnostic quality control data of the local terminal; determining and reporting a location of the local terminal; calculating a Barten curve of the local terminal which may be based on readings from a light metering device; recording an operating status of the local terminal (e.g., powered on, currently displaying diagnostic imagery, etc.); and/or reporting a service history of the local terminal (e.g., last date of inspection or repair). It should be appreciated that this is not an exhaustive list and verification tasks may include the processing of any information that may be useful in analyzing the conditions in which or at which a local terminal is operating. Such information may be beneficial, for example, for verifying compliance with standards, for legal defense of a malpractice claim by establishing a secure record of appropriate image quality and environmental conditions for diagnostics, etc.

At a process 306, a verification report 306, generated based on the verification task, is transmitted to the remote host. The verification report may contain data from the verification task may be generated and transmitted to the remote host 250 for storage and/or analysis. Verification reports may be generated, stored at the local terminal 200, transmitted, and/or stored at the remote host 250 in a secure manner to ensure the integrity of the information therein. In this regard, a proprietary encryption structure or internal protocol may be implemented by the ASIC 210 operating on local terminal 200.

Figure 5:
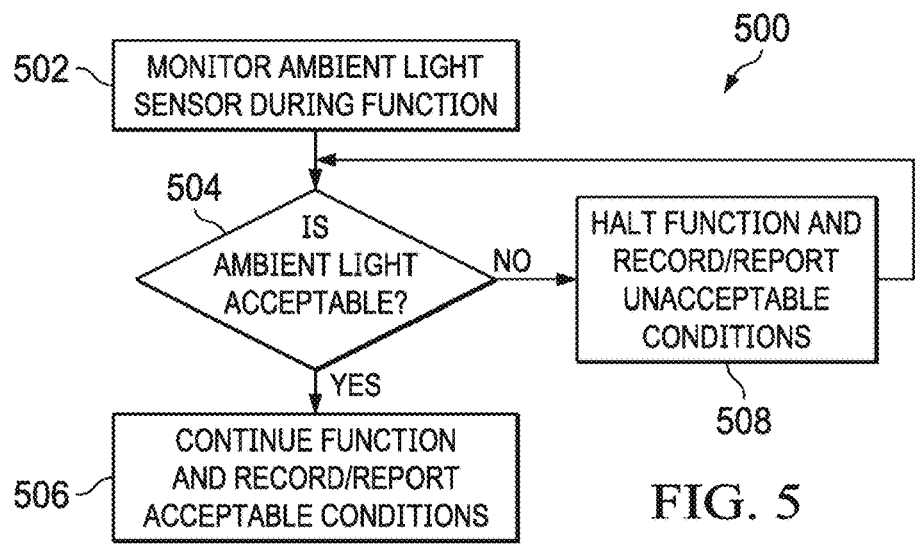
FIG. 5 is a flow chart illustrating a method of remotely verifying conformance with a standard pertaining to an environmental condition of an image presentation device.

FIG. 5 is a flow chart illustrating a method 500 of verifying and reporting a status of conformance with a standard pertaining to an environmental condition of an image presentation device. The method 500 is illustrated as a set of operations or processes, but not all of the illustrated processes may be performed in all embodiments of method 500. Additionally, one or more processes that are not expressly illustrated in FIG. 5 may be included before, after, in between, or as part of the illustrated processes. In some embodiments, one or more of the processes may be implemented, at least in part, in the form of executable code stored on non-transitory, tangible, machine-readable media that when run by one or more processors may cause the one or more processors to perform one or more of the processes. In one or more embodiments, the one or more of the processes may be performed by the local terminal 200, 200A alone or with a remote host 250.

At a process 502, in order to prevent an image presentation device from being operated in unacceptable conditions, an ambient light sensor (e.g., sensor 204, 204A) associated with an image presentation device (e.g., 202, 202A) may monitor ambient lighting. At a process 504, a determination is made as to whether the ambient lighting is acceptable for performing or continuing to perform a function of the local terminal. At a process 508, if the ambient lighting is not acceptable, the terminal application (e.g., terminal application 208) may instruct the ASIC (e.g., ASIC 210) to halt one or more functions of the local terminal. Furthermore, a warning may be presented on the image presentation device or audibly transmitted with a speaker. Additionally or alternatively, the ambient lighting level or an indication thereof may be stored by the ASIC for reporting to the remote host. A verification report pertaining to non-compliant ambient lighting may include the date and time of the non-compliance, the level of ambient lighting, etc. Functions that may be halted by the ASIC include, but are not limited to, monitoring functioning of the image presentation device or calibrating the image presentation device with a light metering device, diagnostic services, etc. After an unacceptable condition is determined at the process 508, the ambient sensor may continue monitoring the ambient light levels at process 504 until they fall back into an acceptable range. When the conditions detected by the ambient sensor are acceptable, at a process 506 the terminal application may allow the function(s) of the local terminal to continue 506. Additionally or alternatively, a record may be generated in the memory chipset that the ambient sensor detected acceptable conditions.

Although described in relation to an ambient light sensor and ambient lighting conditions, it should be appreciated that the verification and reporting described in relation to FIG. 5 may pertain to any condition and any sensor or other means for detecting a condition at the local terminal, for example, noise levels (which may distract a user), location (to prevent HIPAA violations by performing a diagnosis in a public place), etc.

Figure 6:
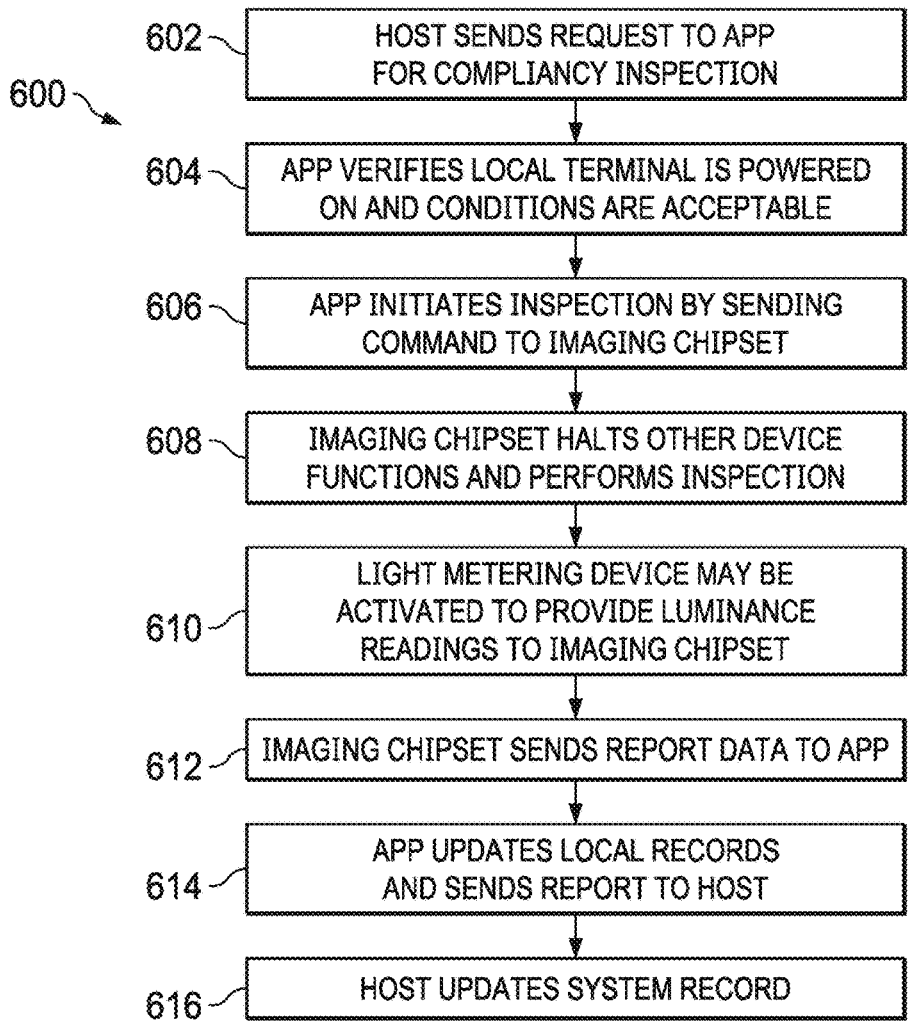
FIG. 6 is a flow chart illustrating a method of remotely reporting an operating condition of an image presentation device.

FIG. 6 is a flow chart illustrating a method 600 of remotely monitoring a local terminal (e.g., a local terminal 200, 200A) by initiating an inspection of an image presentation device (e.g. image presentation device 202, 202A). The method 600 is illustrated as a set of operations or processes, but not all of the illustrated processes may be performed in all embodiments of method 600. Additionally, one or more processes that are not expressly illustrated in FIG. 6 may be included before, after, in between, or as part of the illustrated processes. In some embodiments, one or more of the processes may be implemented, at least in part, in the form of executable code stored on non-transitory, tangible, machine-readable media that when run by one or more processors may cause the one or more processors to perform one or more of the processes. In one or more embodiments, the one or more of the processes may be performed by the local terminal 200, 200A alone or with a remote host 250.

Method 600 describes in greater detail verification and reporting that may be performed, specifically related to ambient lighting. During a diagnosis using images viewed on an image presentation device, it is important that ambient lighting at the location of the local terminal is appropriate for optimal viewing. For example, bright ambient lighting (e.g., direct sunlight) may overpower the brightness of the image presentation device such that a user is unable to view the images on the image presentation device with sufficient clarity. That is, for example, if a doctor cannot clearly view medical images on the image presentation device during the process of diagnosing a condition, there is a risk that a misdiagnosis may occur. Accordingly, standards provide for optimal or acceptable ambient conditions in which diagnostics are to be performed. In order to prevent a diagnosis from being conducted in unacceptable conditions, an ambient light sensor associated with an image presentation device may monitor ambient lighting. If the ambient lighting is not acceptable, the terminal application may conceal or close windows displaying images and provide a warning to the user that the conditions are not compliant with acceptable standards or practices. Further, the ambient lighting level or an indication thereof may be stored by the ASIC for reporting to the remote host. A verification report pertaining to non-compliant ambient lighting may include records of the patient being diagnosed, the images being viewed, the date and time of the non-compliance, etc. The ambient sensor may continue monitoring the ambient light levels until they fall back into an acceptable range. When the conditions detected by the ambient sensor are acceptable, the terminal application may allow the image presentation device to continue or resume displaying the images for diagnosis. Additionally or alternatively, a record may be generated in the memory chipset that the ambient sensor detected acceptable conditions.

At a process 602, a remote host sends a verification instruction requesting a compliance inspection that is received by a local terminal, and more specifically by a terminal application running on the local terminal, via a communications network such as the Internet. At a process 604, the terminal application verifies the local terminal is powered on and that conditions are acceptable. For example, the terminal application may turn the local terminal on, toggle the local terminal into DICOM mode, and may perform the ambient lighting verification described in relation to FIG. 5. The terminal application, optionally, stores the request, or a portion thereof in local memory, sets a calendar entry to initiate the inspection at a time indicated by the request, and sends confirmation that the inspection has been scheduled to the remote host. In some instances, the request may indicate the inspection is to occur immediately such that a calendar entry is not required.

At a process 606, the terminal application instructs the imaging chipset to initiate the inspection at the scheduled time. At a process 608, the imaging chipset establishes communication with a light metering device coupled to the local terminal. In embodiments in which the entire display area of the image presentation device is used to produce a test output, the imaging chipset may ensure the local terminal is in the appropriate operating mode for the verification (e.g., a DICOM mode). In embodiments in which a test window is produced on only a small portion of the display area of the image presentation device, the local terminal may continue operating in a normal mode while the verification task occurs or may toggle a compliance-related (e.g., DICOM) operating mode. At a process 610, the light metering device provides luminance readings via a feedback signal to the imaging chipset as the test array of light sensors in the light metering device scans the image presentation device. The terminal application is able to cause a portion of the image presentation device to produce a first test output including a grayscale test pattern ranging from darkest shades to brightest shades designed for determining whether the image presentation device conforms to the standard. The light metering device is couplable to the image presentation device to capture the light characteristic of the first test output emitted directly by the image presentation device. In some embodiments, a test window presenting the first test output of the image presentation device is dragged across the array of light sensors, which may be done automatically or at the direction of a user input device (e.g., mouse). The ASIC is configured to determine whether the captured light characteristic, as reported in the feedback signal, conforms to the standard. At a process 612, based on the feedback signal from the light metering device, the imaging chipset generates a verification report which is received by the terminal application. At a process 614, the report may be stored locally on the local terminal and/or transmitted to the remote host. The verification report may include an indication that the image presentation device is in compliance with the respective standard or that the image presentation device is out of compliance. At a process 616, based on the verification report, the remote host may update a system record in which verification data from the local terminal is aggregated.

Figure 7:
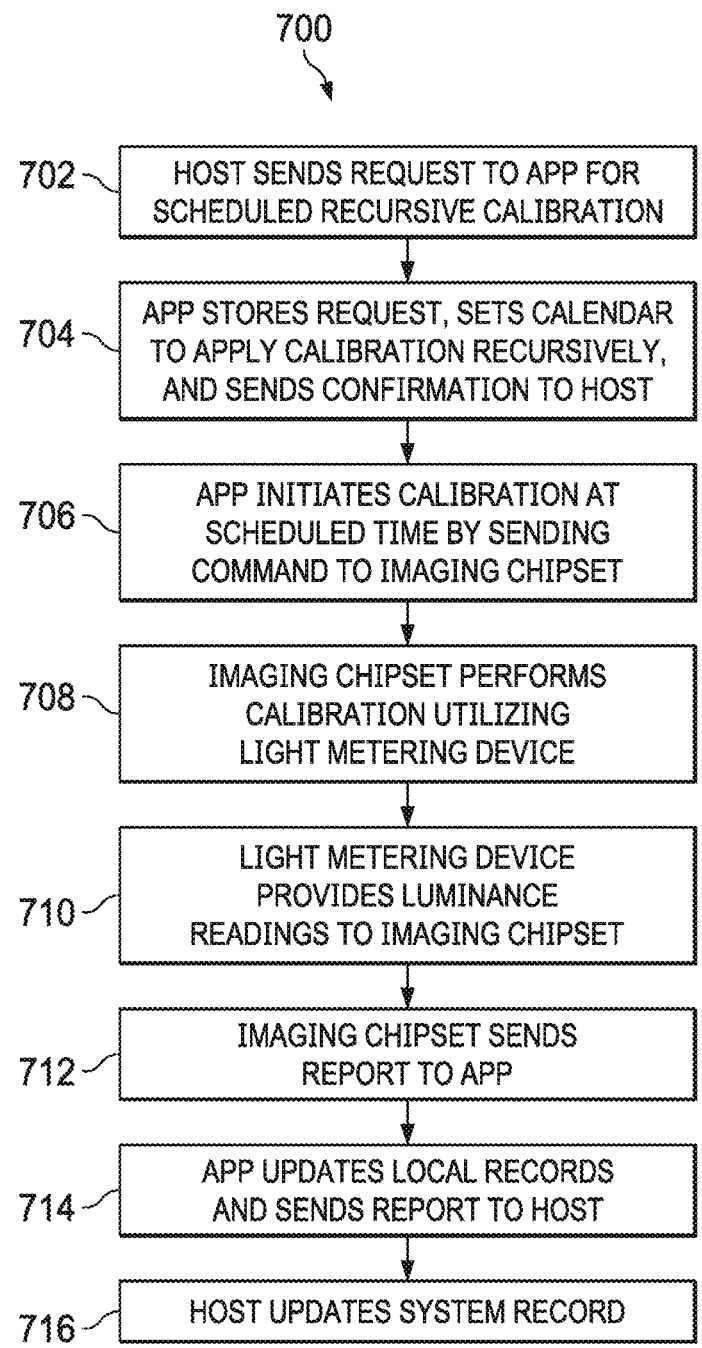
FIG. 7 is a flow chart illustrating a method of remotely calibrating an image presentation device.

FIG. 7 is a flow chart illustrating a method 700 of remotely calibrating an image presentation device. The method 700 is illustrated as a set of operations or processes, but not all of the illustrated processes may be performed in all embodiments of method 700. Additionally, one or more processes that are not expressly illustrated in FIG. 7 may be included before, after, in between, or as part of the illustrated processes. In some embodiments, one or more of the processes may be implemented, at least in part, in the form of executable code stored on non-transitory, tangible, machine-readable media that when run by one or more processors may cause the one or more processors to perform one or more of the processes. In one or more embodiments, the one or more of the processes may be performed by the local terminal 200, 200A alone or with a remote host 250.

At a process 702, a remote host sends a verification instruction requesting recursive calibration that is received by a local terminal, and more specifically by a terminal application running on the local terminal, via a communications network such as the Internet. At a process 704, the terminal application stores the request, or a portion thereof in local memory, sets a calendar entry to initiate the calibration at a time indicated by the request, and sends confirmation that the calibration has been scheduled to the remote host. In some instances, the request may indicate the calibration is to occur immediately such that a calendar entry is not required. This may be the case if a previously transmitted verification report indicates the image presentation device of the local terminal is out of compliance, which may be case following an inspection as described in relation to FIG. 6. In such an instance, the verification instruction may also include an indication that use of the image presentation device is to be restricted until the calibration has successfully been performed and confirmed. For example, the terminal application, in conjunction with the imaging chipset, may prevent diagnostic imaging from being displayed on the local terminal but may allow non-diagnostic applications (e.g., email or web browsing) to continue.

At a process 706, the terminal application instructs the imaging chipset to initiate the calibration at the scheduled time and ensure the image presentation device is operating in a desired operating mode. In embodiments in which the entire display area of the image presentation device is used to produce a test output, the imaging chipset may ensure the local terminal is in the appropriate operating mode for the verification (e.g., a DICOM mode). In embodiments in which a test window is produced on only a small portion of the display area of the image presentation device, the local terminal may continue operating in a normal mode while the verification task occurs or may toggle a compliance-related (e.g., DICOM) operating mode. At a process 708, the imaging chipset may establish communication with a light metering device 708. At a process 710, the light metering device provides luminance readings via a feedback signal to the imaging chipset as the test array of light sensors in the light metering device scans the image presentation device. The terminal application is able to cause a portion of the image presentation device to produce a first test output including a grayscale test pattern across a range of brightnesses designed for determining whether the image presentation device conforms to the standard. The light metering device is couplable to the image presentation device to capture the light characteristic of the first test output emitted directly by the image presentation device. The ASIC is configured to determine whether the captured light characteristic, as reported in the feedback signal, conforms to the standard. At a process 712, based on the feedback signal from the light metering device, the imaging chipset generates a verification report which is received by the terminal application. At a process 714, the terminal application updates and stores local records on the local terminal and/or transmits to the remote host. The verification report may include a lookup table which is stored locally in response to a calibration, such as in EEPROM or other memory of the ASIC, for reference by the imaging chipset when operating in a specified operating mode such as DICOM mode to ensure compliance with a standard. That is, the lookup table may include values that are referenced by the ASIC to produce grayscale shades in accordance with the results of the most recent calibration. At a process 716, based on the verification report, the remote host may update a system record in which verification data from the local terminal is aggregated for subsequent review or analysis.

Figure 8:
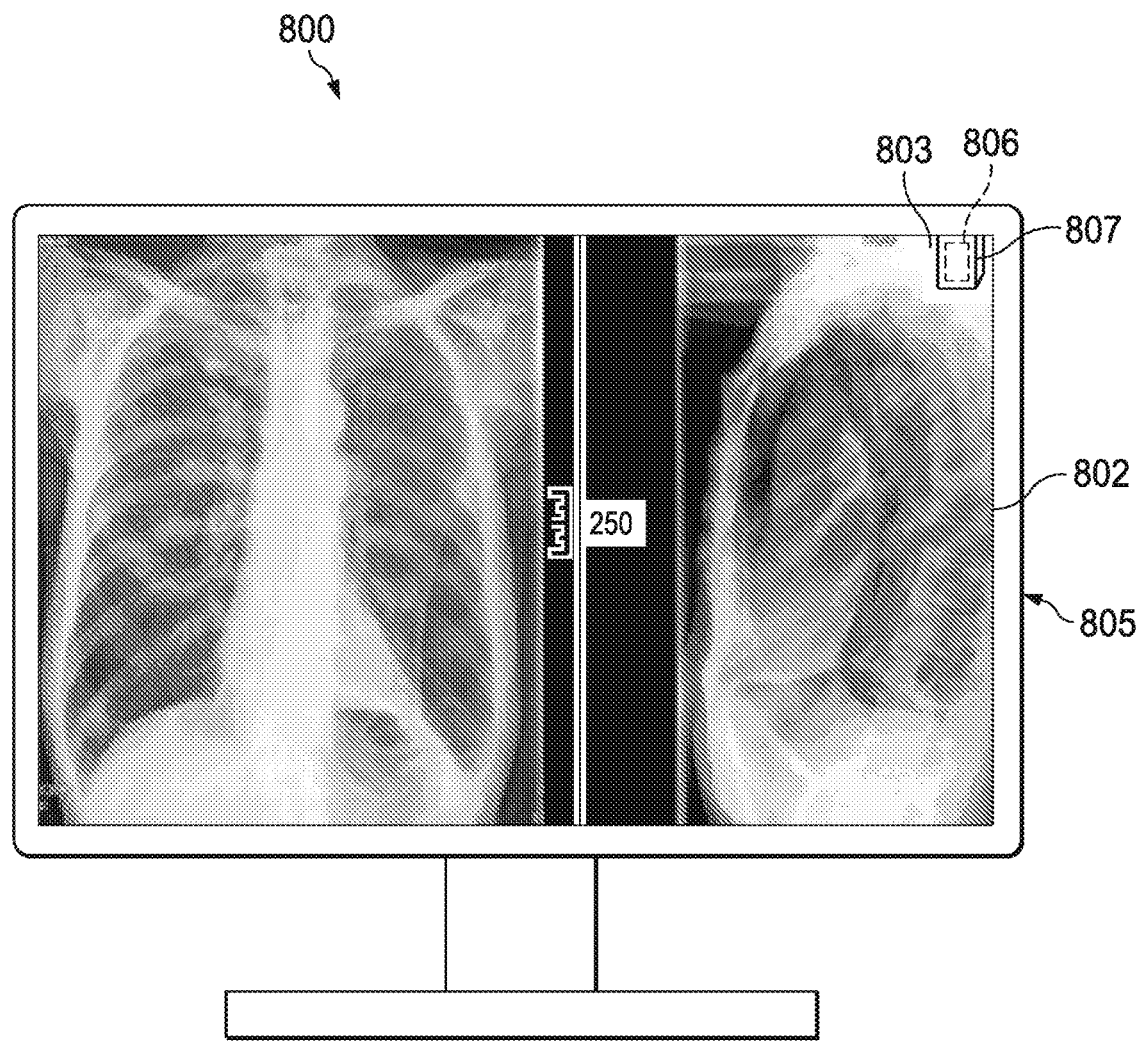
FIG. 8 illustrates an embodiment of a local terminal image presentation device with an integrated light metering device.

FIG. 8 illustrates a local terminal 800 that includes an image presentation device 802 in the form of a display device. In this embodiment, local terminal 800 may comprise an all-in-one computer built into a monitor housing 805. The local terminal may be similar to any of the previously described local terminals with the differences as described. Extending from a corner of the housing 805 is an extension housing 807 in which an embedded light metering device 806 is positioned. The extension housing 807 may be integrated or integrally formed with the monitor housing 805 or may be coupled to the monitoring housing 805 by a mechanical or adhesive coupling. The light metering device 806 may be integrally formed with the extension housing 807, may be flush mounted on the housing 807, or may project outward from a surface of the housing 807. The light metering device 806 may include components, such as wires or cables, that extend within the housing 805 to connect with the ASIC (e.g., ASIC 210) of the local terminal 800. The light metering device 806 may be coupled to the ASIC of the local terminal 800 with UART communication or other suitable connection. In alternative embodiments, the light metering device may be wirelessly connected to the ASIC of the local terminal 800. In alternative embodiments, the light metering device 806 may be positioned at another position over the image presentation device 802 that may be relatively inconspicuous to a viewer of the image presentation device 802.

The light metering device may function similar to the light metering devices previously described herein, with differences as described. In this embodiment, the light metering device 806 is disposed over a test window 803 displayed on the image presentation device 802 which may extend slightly beyond the testing area of the light metering device 806. In the illustration, the dimensions of the test window 803 have been exaggerated for clarity. In some embodiments, the test window may comprise a strip extending across a portion of the image presentation device, a portion of the image presentation device, or the entire display area of the image presentation device. As described below, the test window portion 803 of the image presentation device 802 may operate in a different presentation mode than the remainder of the area of the image presentation device 802.

In the illustrated embodiment, light metering device 806 may be used to complete a verification task invoked by a remote host to, for example, calibrate or monitor the image presentation device 802 using information sensed from the test window 803. The verification tasks may be performed in an unobtrusive manner without interrupting the use of the image presentation device 802 for presenting medical images to a viewer at the local terminal 800 or performing other tasks. In many cases, a local viewer of the local terminal 800 may not even be aware that calibration or monitoring is occurring. Moreover, with an embedded light metering device 806, verification procedures may be remotely initiated at any time that the local terminal 800 is powered on and connected to a network for communication with a remote host because the light metering device 806 is always properly positioned at the image presentation device 802 whenever verification tasks are needed, without user intervention to couple a light metering device to the image presentation device.

In some embodiments, a light metering device may be mounted internally in a local terminal, for example between an image producing layer, such as an LCD module, and a protective layer, such as polarizing film or a glass panel. In some embodiments, the light metering device may even be concealed behind a bezel or other structure of the local terminal such that it is out-of-view from a user. In this regard, the image presentation device, or a small portion thereof, may extend behind the bezel at the location of the light metering device. A test window may be presented on this small portion of the image presentation device which is concealed such that calibration and monitoring may occur continuously or periodically without interruption to use of the unconcealed portion of the image presentation device. In this regard, use of an image presentation device may be continuous until a monitoring process by the light metering device identifies that the image presentation device has fallen out of compliance with a standard, at which point the ASIC may halt certain functions of the device.

A local terminal, such as the local terminal 800 of FIG. 8, may be operable in a plurality of operating modes. In this regard, a button or switch may be provided on the local terminal for toggling between operating modes. Additionally or alternatively, a remote host may send a verification instruction to a local terminal that prompts the local terminal to enter or exit a certain operating mode.

A DICOM mode may be included in a local terminal (e.g. local terminal 800) in which the ASIC is operative to control operations of at least a portion of the image presentation device (e.g., a test window portion) to ensure compliance with DICOM requirements (or another standard). Additionally, a local terminal may include a normal operating mode in which display data is passed through the ASIC in a low-performance state which does not require the stringent controls of DICOM-compliant processing or bypasses the ASIC. In this regard, a user display portion of the display area of the image presentation device, which does not include the test window portion, may operate in a normal mode or a DICOM mode regardless of the current mode the test window. The user display portion of the display area of the presentation device may include the remainder of the display area (i.e., the display area other than the test window portion). DICOM mode may also be mandatory during use of the remainder of the display area for certain applications or functions, such as when a medical diagnosis is being performed. Calibration, monitoring, or other verification tasks may be performed when the test window is in DICOM mode and the remainder of the display area of the image presentation device is operating in the DICOM or the normal operating mode.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Although described in the context of medical imaging, it will be appreciated that the utilities described herein may be utilized for a variety of imaging contexts including, inter alia, identifying a material composition of an object, determining the internal construction of an object or structure, and a wide variety of other purposes benefiting from conformance to a predetermined standard.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a local terminal in operative communication with a remote host, the local terminal including:
an image presentation device;
an application-specific integrated circuit ("ASIC"); and
a terminal application in communication with the ASIC, the terminal application configured to initiate a verification task, via the ASIC, pertaining to an operating condition of the image presentation device and to communicate a verification report about a result of the verification task to a remote host, wherein the local terminal further comprises or is coupled to an ambient sensor configured to monitor ambient lighting, and wherein the operating condition of the image presentation device includes a luminance of ambient lighting at the local terminal.

2. The system of claim 1, wherein the verification task comprises:
retrieving a record from a memory module at the local terminal, the record indicating the operating condition and a time the operating condition was recorded; and
generating the verification report, the verification report including the record; and wherein the terminal application communicates the verification report to the remote host using internet protocol through at least one network.

3. The system of claim 1, wherein the verification task comprises:
detecting the operating condition at the local terminal; and
assembling the verification report based on the detecting; and
wherein the terminal application communicates the verification report to the remote host using internet protocol through at least one network.

4. The system of claim 3, wherein the verification task is performed in accordance with a standard.

5. The system of claim 4, wherein the standard is a Digital Imaging and Communications in Medicine ("DICOM") standard.

6. The system of claim 4, wherein the ASIC is configured to disable one or more functions of the image presentation device based on the ambient lighting luminance being non-compliant with the standard.

7. The system of claim 6, wherein the one or more functions includes displaying a medical image to a user for making a diagnosis based on the medical image.

8. The system of claim 6, wherein the local terminal further comprises or is couplable to a light metering device which includes a test array of light sensors.

9. The system of claim 8, wherein the operating condition includes a light characteristic of the image presentation device, wherein the terminal application is able to cause a portion of the image presentation device to produce a first test output including a grayscale test pattern designed for determining whether the image presentation device conforms to the standard, wherein the light metering device is configured to capture the light characteristic of the first test output emitted directly by the image presentation device, wherein the ASIC is configured to determine whether the captured light characteristic conforms to the standard.

10. The system of claim 9, wherein the verification task further comprises calibrating the image presentation device in response to the captured light characteristic of the first test output.

11. The system of claim 10, wherein the light characteristic comprises a luminance of the image presentation device.

12. The system of claim 11, wherein the verification task is performed in response to receipt of a verification instruction sent from the remote host and received by the terminal application indicating a scheduled time for performance of the verification task.

13. The system of claim 11, wherein the verification task is automatically performed on a periodic basis.

14. The system of claim 9, wherein the local terminal further includes a housing, wherein the light metering device is housed with the housing, and wherein the light metering device overlaps the portion of the image presentation device configured to produce the first test output.

15. The system of claim 3, wherein the operating condition comprises at least one of:
a usage history of the local terminal;
diagnostic quality control data of the local terminal;
a location of the local terminal;
a Barten curve of the local terminal;
an operating status of the local terminal;
a power status of the local terminal; or
a service history of the local terminal.

16. The system of claim 15, wherein the remote host is in operative communication with at least the local terminal and a second local terminal, and wherein the remote host is configured to store verification reports from both the local terminal and the second local terminal.

17. A method, comprising:
providing a local terminal in operative communication with a remote host, the local terminal including:
an image presentation device;
an application-specific integrated circuit ("ASIC"); and
a terminal application stored at the local terminal and operable to provide instructions to the ASIC;
receiving a verification instruction from the remote host at the local terminal;
performing, via the ASIC and in response to the verification instruction, a verification task on the local terminal, the verification task pertaining to an operating condition of the image presentation device, wherein the operating condition includes a luminance of the image presentation device detected by a light metering device included in or coupled to the local terminal; and
transmitting a verification report based on a result of the verification task to the remote host via at least one network using internet protocol.

18. The method of claim 17, wherein the performing the verification task comprises:
detecting the operating condition at the local terminal; and
assembling a verification report based on the operating condition.

19. The method of claim 18, wherein the verification task allows for remotely verifying that the image presentation device conforms to a standard and securely storing the result of the verification task.

20. The method of claim 19, wherein the light metering device includes a test array of light sensors, and wherein the operating condition includes a luminance of the image presentation device detected by the test array.

21. The method of claim 20, wherein the verification task further comprises:
causing a portion of the image presentation device to produce a first test output including a grayscale test pattern designed for determining whether the image presentation device conforms to the standard, the causing being performed by the terminal application;

capturing a light characteristic of the first test output, emitted directly by the image presentation device, with the light metering device coupled to the image presentation device;

determining whether the captured light characteristic conforms to the standard; and calibrating the image presentation device in response to the captured light characteristic of the first test output.

22. The method of claim 21, wherein the local terminal further comprises an ambient sensor, wherein the operating condition includes an ambient lighting luminance detected by the ambient sensor, and wherein the verification task further includes:

disabling, with the ASIC and in response to the ambient lighting luminance being non-compliant with the standard, one or more functions of the image presentation device.

23. The method of claim 18, wherein the operating condition comprises at least one of:

a usage history of the local terminal;
diagnostic quality control data of the local terminal;
a location of the local terminal;
a Barten curve of the local terminal;
an operating status of the local terminal;
a power status of the local terminal; or
a service history of the local terminal.

* * * * *